(12) United States Patent
Dawson et al.

(10) Patent No.: US 9,433,207 B2
(45) Date of Patent: Sep. 6, 2016

(54) NON-IONIC SURFACTANT AGGREGATES

(75) Inventors: Howard Bernard Dawson, Derby (GB); Martin Balderstone, Derby (GB)

(73) Assignee: ENVIROQUEST RESEARCH LIMITED, Buckinghamshire (GB)

(*) Notice: Subject to any disclaimer, the term of this patent is extended or adjusted under 35 U.S.C. 154(b) by 1496 days.

(21) Appl. No.: 11/576,795

(22) PCT Filed: Oct. 7, 2005

(86) PCT No.: PCT/GB2005/003860
§ 371 (c)(1),
(2), (4) Date: Aug. 13, 2007

(87) PCT Pub. No.: WO2006/038019
PCT Pub. Date: Apr. 13, 2006

(65) Prior Publication Data
US 2008/0096763 A1 Apr. 24, 2008

(30) Foreign Application Priority Data

Oct. 9, 2004 (GB) .................................. 0422470.5
Apr. 1, 2005 (GB) .................................. 0506617.0

(51) Int. Cl.

| | | |
|---|---|---|
| *A01N 25/30* | (2006.01) | |
| *C11D 1/825* | (2006.01) | |
| *C11D 3/48* | (2006.01) | |
| *C11D 1/72* | (2006.01) | |
| *B27K 3/50* | (2006.01) | |
| *C11D 1/74* | (2006.01) | |
| *C11D 1/52* | (2006.01) | |
| *C11D 1/44* | (2006.01) | |
| *A01N 53/00* | (2006.01) | |
| *A01N 47/34* | (2006.01) | |
| *A01N 47/12* | (2006.01) | |
| *A01N 43/653* | (2006.01) | |
| *A01N 43/30* | (2006.01) | |
| *A01N 43/40* | (2006.01) | |

(52) U.S. Cl.
CPC ............... *A01N 25/30* (2013.01); *C11D 1/825* (2013.01); *C11D 3/48* (2013.01); *B27K 3/50* (2013.01); *C11D 1/44* (2013.01); *C11D 1/528* (2013.01); *C11D 1/72* (2013.01); *C11D 1/74* (2013.01)

(58) Field of Classification Search
None
See application file for complete search history.

(56) References Cited

U.S. PATENT DOCUMENTS

| | | | | |
|---|---|---|---|---|
| 5,037,653 | A | * | 8/1991 | Dawson ........................ 424/405 |
| 5,283,229 | A | | 2/1994 | Narayanan et al. |
| 5,558,806 | A | | 9/1996 | Policello et al. |
| 5,912,220 | A | * | 6/1999 | Sramek et al. ............... 510/284 |
| 6,045,816 | A | * | 4/2000 | Narayanan et al. .......... 424/405 |
| 2003/0125211 | A1 | | 7/2003 | Woznica et al. |

FOREIGN PATENT DOCUMENTS

| | | | | |
|---|---|---|---|---|
| EP | 0394847 | | 10/1990 | |
| GB | 1524037 | * | 9/1978 | ............. A01N 17/10 |
| JP | 6316502 | | 11/1994 | |
| WO | 9949008 | | 9/1999 | |

OTHER PUBLICATIONS

Goodman group pluronic 131 [online] retrieved from the internet on May 13, 2010 from: http://www-jmg.ch.cam.ac.uk/data/molecules/misc/l31.html; Jun. 29, 2006; 3 pages.*
Wikipedia (en.wikipedia.org/wiki/Hydrophilic-lipophilic_balance, last visit Oct. 4, 2013).*
Rodia, "Alkamuls EL 620", (rhodia.com/en/markets_and_products/product_finder/product_details.tcm?productCode=90001918&productName=ALKAMULS+EL+620, last visit Sep. 30, 2013).*
Rodia, "Antarox L-61", (rhodia.com/en/markets_and_products/product_finder/product_details.tcm?productCode=90017144&productName=ANTAROX+L-61, last visit Sep. 30, 2013).*
Robert, "Diverse applications of N-alkyl pyrrolidones", Specialty Chemicals Magazine Jul./Aug. 2002, pp. 15-16.*
Basf, "Pluronic L31 Block Copolymer Surfactant", (2004): [retreived on Nov. 17, 2014 from on-line website http://worldaccount.basf.com/wa/NAFTA/Catalog/ChemicalsNAFTA/doc4/BASF/PRD/30085851/.pdf?title=&asset_type=pi/pdf&language=EN&urn=urn:documentum:eCommerce_sol_EU:09007bb28001f6f6.pdf].*
On-line Merriam-Webster dictionary: retreived from on-line website http://www.merriam-webster.com/dictionary/particle, (last visit Apr. 25, 2015)].*
Solans et al., "Industrial Applications of Microemulsions", Marcel Dekker, Inc., 1997, pp. 1-424 (only p. 75 is attached).*
Foy et al., "Pesticide formulation and adjuvant technology", CRC press, 1996, pp. 1-384 (only p. 150 is attached).*

* cited by examiner

*Primary Examiner* — Ernst V Arnold
*Assistant Examiner* — Kyung Sook Chang
(74) *Attorney, Agent, or Firm* — Chernoff, Vilhauer, McClung & Stenzel, LLP

(57) ABSTRACT

A non-ionic surfactant aggregate comprises a water insoluble biocidally active ingredient, a non-ionic surfactant system, and water. The non-ionic surfactant system comprises first and second non-ionic surfactants.

22 Claims, No Drawings

NON-IONIC SURFACTANT AGGREGATES

This is a national stage application filed under 35 USC 371 based on International Application No. PCT/GB2005/003860 filed Oct. 7, 2005, and claims priority under 35 USC 119 of United Kingdom Patent Application No. 0422470.5 filed Oct. 9, 2004 and United Kingdom Patent Application No. 0506617.0 filed Apr. 1, 2005.

This invention relates to non-ionic surfactant aggregates. More particularly, but not exclusively, the invention relates to mixed non-ionic surfactant aggregates. The invention also relates to methods of solubilising water insoluble ingredients, and the packaging of products incorporating such aggregates. Embodiments of the invention relate to formulations and methods whereby specific aggregate structures can be made in order to accommodate water containing mixtures into packaging made from water soluble films such as polyvinyl alcohol (PVA).

Pesticide formulations are normally prepared as concentrated products which are then diluted in water prior to their application by a variety of techniques (e.g. spray, mist, fog etc.), onto a variety of surface types (e.g. plants, hard surfaces, fabrics etc) to give protection against a wide range of target pests (eg. insects, fungal infections, weeds etc). In the majority of cases the actual active component is not soluble in water to any appreciable extent and a number of formulation types are required in order to achieve active ingredient concentrations at appreciable, and as a consequence commercially viable, levels.

Traditionally the formulations used can be of three main general types:
(a) Emulsifiable Concentrates and Oil in Water Emulsions The active ingredient is dissolved in hydrocarbon solvent with a blend of surfactants to produce the emulsifiable concentrate (EC) which is then diluted with water prior to use to produce an oil in water emulsion. Alternatively the EC can be partially diluted to give an oil in water emulsion concentrate (EW) which is then further diluted with water prior to use.
(b) Suspension Concentrates (Flowables)

The ai is ground into a fine form and suspended in a liquid base (oil or water) using a range of additives such as dispersants (surfactants), thickening agents, preservatives and anti freeze (water based) so that when added to water the ai is in the form of finely suspended particles. These types of formulation can be combined with emulsions (EW) to form suspo-emulsions.
c) Solid Formulations Wettable Powders (WP) consist of an inert powder impregnated with the active ingredient which is then milled to a small and evenly distributed particle size. The dispersion of the powder upon dilution in water is aided by the incorporation of wetting agents and dispersants (surfactants) into the formulation. There are a number of variations on this basic theme (e.g. water dispersible granules etc).

Whilst the use of these formulation types is well established for a diverse range of application types (eg. crop protection, vector control, public hygiene and pest control, timber treatment, home and garden, professional grounds care, termite control etc) there are inherent weaknesses with all formulation types. The Suspension Concentrates (SC) and Wettable Powders require significant processing costs associated with the milling of the solid component, the EC and EW formulations contain organic solvents which can be hazardous both to the user and the Environment. Moreover, all these formulations, when diluted with water, show a propensity to phase separate either by sedimentation (SC and WP) or by creaming (EC and EW) and in the case of the SC and EW types this phase separation can also occur in the concentrates.

The degree of phase separation can be very significant and this is illustrated in table 1 below where the level of separation was determined analytically by HPLC, for a range of conventional formulations containing synthetic pyrethroid insecticides as the active ingredient following their dilution with water.

Dilutions were prepared and mixed thoroughly at which point samples were taken and the nominal active ingredient content determined analytically. The dilutions were then allowed to stand for four hours and further samples taken from the top, middle and bottom 10% fractions and the active ingredient content determined and expressed as a fraction of the nominal value.

TABLE 1

Phase Separation following dilution

| | EC Formulation | EW Formulation |
|---|---|---|
| nominal ai content (wt %) | 0.067 | 0.0127 |
| ai content in Top 10% | 0.119 | 0.0044 |
| (ai) actual/nominal | 1.78 | 0.35 |
| ai content in Middle 10% | 0.030 | 0.0045 |
| (ai) actual/nominal | 0.45 | 0.35 |
| ai content in Bottom 10% | 0.025 | 0.0500 |
| (ai) actual/nominal | 0.30 | 3.94 |

This phase separation can give rise to problems in two different aspects of performance:
(a) where (ai) actual/nominal is <<1 the level of biological control of the pest is low; and
(b) where (ai) actual/nominal is >>1 the toxicological risk to both operator and environment is high.

According to one aspect of this invention, there is provided a non-ionic surfactant aggregate comprising a water insoluble ingredient, a non-ionic surfactant system and water. The preferred embodiment of the non-ionic surfactant aggregate comprises a mixed non-ionic surfactant aggregate.

According to another aspect of this invention there is provided a method of solubilising a water insoluble ingredient comprising mixing a water insoluble ingredient with a non-ionic surfactant system and water to provide a non-ionic surfactant aggregate in which the water insoluble ingredient is solubilised therein.

The non-ionic surfactant aggregate may comprise one or more water insoluble ingredients. The, or each, water insoluble ingredient is preferably an organic substance. The water insoluble ingredient is preferably an active ingredient, preferably a biologically active ingredient, such as a biocide. The active ingredient may comprise a pesticide. The active ingredient may comprise one or more of a herbicide, a fungicide, an insecticide, a nematicide and a miticide.

One advantage of the preferred embodiments of this invention is that mixed non-ionic surfactant aggregates containing high levels of active ingredient or ingredients can be diluted with water to produce a thermodynamically stable mixed non-ionic surfactant aggregate. Such mixed non-ionic surfactant aggregates have no tendency to phase separate across a broad range of temperatures (typically 0-50° C.) at a wide range of water hardness (typically 0-1000 ppm calcium carbonate).

The active ingredient may comprise an insecticide, which may comprise one or more of: pyrethroids, such as a synthetic pyrethroid; an organophosphate compound, such as chlorpyrifos-ethyl, chlorpyrifos-methyl, pirimiphos-methyl, fenitrothion; a phenyl ether such as pyriproxyfen; a benzoylurea, such as flufenoxuron; a carbamate, such as fenoxycarb, carbosulfan; nicotinoids, such as acetamiprid; pyridinecarboxamides, such as flonicamid; and/or others. The pyrethroid may be selected from one or more of bifenthrin, zeta-cypermethrin, alpha-cypermethrin, tetramethrin, lambda-cyhalothrin, fenvalerate, cyfluthrin, bioresmethrin, permethrin, delta-methrin.

The active ingredient may comprise a fungicide which may be selected from one or more of a conazole compound, such as azaconazole, cyproconazole, propiconazole, tebuconazole; carbamates such as IPBC (3-iodo-2-propynyl-butyl-carbamate); and/or others.

The active ingredient may comprise a herbicide which may be selected from the triazolinone compounds such as carfentrazone-ethyl, the aryl triazolinone compounds such as sulfentrazone or the phosphonic acid compounds such as glyphosate. These can be mixed with plant growth regulators such as Ethephon.

The non-ionic surfactant system may comprise a single non-ionic surfactant, but preferably, the non-ionic surfactant system comprises first and second non-ionic surfactants. The first non-ionic surfactant may be more soluble in oil than in water, (having a low hydrophilic-lipophilic balance [HLB]) and the second non-ionic surfactant may be more soluble in water than in oil (having a high HLB).

Preferably, the first and second non-ionic surfactants have different hydrophilic-lipophilic balances to each other.

The non-ionic surfactant system may comprise greater than two non-ionic surfactants.

In some embodiments where there are mixtures of water insoluble active ingredients, the blend of non-ionic surfactants required to provide the desired level of stability (as a concentrate or as a dilution in water) can be complex.

The non-ionic surfactant system may comprise one or more of alkoxylated alcohols, amine ethoxylate, ester ethoxylate, castor oil ethoxylate, fatty acid ethoxylate, amide ethoxylate, ethylene oxide-propylene oxide block copolymers, alkoxylated oils, such as alkoxylated vegetable oils, alkoxylated fatty acids, alkylomide ester or food ester.

The aggregate may be substantially free of ionic surfactants. As used herein the term "substantially free of" is intended to encompass the situation where small amounts are present, but these amounts do not substantially affect the properties or characteristics of the aggregate.

The alkoxylated alcohols may comprise an alcohol ethoxylate. The alkoxylated alcohol may have a straight or branched chain. The alkoxylated alcohol may be any chain length but preferred chain lengths, are 8 to 18 carbon atoms, more preferably 9 to 13 carbon atoms. The alkoxylated alcohol may comprise 1 to 50 moles of ethylene oxide per molecule, preferably 1 to 20 moles ethylene oxide per molecule, and more preferably 2 to 12 moles ethylene oxide per molecule.

The ethylene oxide-propylene oxide block copolymer may have an ethylene oxide content in the range of 10 wt % to 80 wt %. Preferably, the ethylene oxide-propylene oxide block copolymer has an ethylene oxide content in the range of 10 wt % to 40 wt %, more preferably in the range of 10 wt % to 20 wt %. Ethylene oxide propylene oxide block copolymers having a higher ethylene oxide than propylene oxide content are more soluble in water than in oil, (ie. have a high HLB value). Conversely, ethylene oxide-propylene oxide block copolymers having a higher propylene oxide than ethylene oxide content are more soluble in oil than in water (ie. have a low HLB value).

The ethylene oxide-propylene oxide block copolymers used in the preferred embodiment of this invention may comprise molecules with a propylene oxide backbone with ethylene oxide end groups. With such block copolymers, the size of the propylene oxide backbone and the amount of ethylene oxide in the molecule allow for a wide range of variations in terms of water solubility (as shown by aqueous Cloud Points). Hence, they can be used either as primary surfactants (where the ethylene oxide content is 20% or above) or cosurfactants (where the ethylene oxide content is typically 10%).

In the preferred embodiment, ethylene oxide-propylene oxide block copolymers having an ethylene oxide content of less than substantially 20 wt % have a low HLB value. Such block copolymers have, in the preferred embodiments, a propylene oxide backbone, and the HLB value can be modified by altering the molecular weight of the propylene oxide backbone.

The alkoxylated vegetable oil may comprise alkoxylated castor oil. The alkoxylated castor oil may comprise an ethoxylated castor oil. The ethoxylated castor oil may have an ethylene oxide content of 5 to 200 moles ethylene oxide per molecule, preferably 5 to 100 moles ethylene oxide per molecule, more preferably 5 to 60 moles ethylene oxide per molecule.

The non-ionic surfactant aggregate may be provided in one of a plurality of structures, such as a micellar solution, (which may comprise normal or inverted micelles), an oil in water ("water external") microemulsion, a water in oil ("oil external") microemulsion, or a molecular cosolution. These mixed non-ionic surfactant aggregates can also take the form of viscous gels which may be comprised of liquid crystals, and may contain hexagonal, lamella, cylindrical or spherical structures.

The preferred embodiments of the invention have the advantage of enabling a water insoluble ingredient eg. a pesticide, to be solubilised in water, by means of a non-ionic surfactant system, to form a mixed non-ionic surfactant aggregate.

The water insoluble ingredient may be present in the aggregate in an amount in the range of 0.001 wt % to 50 wt %, preferably 0.001 wt % to 40 wt %.

In a first embodiment, the water insoluble ingredient may be present in the non-ionic surfactant aggregate in an amount in the range of 0.1 wt % to 40 wt %, preferably 1 wt % to 40 wt %, more preferably 2 wt % to 40 wt %. This embodiment may comprise a water in oil aggregate such as a lipophilic mixed non-ionic surfactant aggregate, which may comprise a water in oil microemulsion, a micellar solution or a cosolution.

In a second embodiment, the water soluble ingredient may be present in the aggregate in an amount in the range of 0.1 wt % to 35 wt %, preferably 1 wt % to 30 wt %, more preferably 2 wt % to 25 wt %. This embodiment may comprise a mixed non-ionic surfactant aggregate, which may comprise a hexagonal, lamella, cylindrical or spherical structure.

In a third embodiment, the water insoluble ingredient may be present in the aggregate in an amount in the range of 0.001 wt % to 20 wt %, preferably 0.001 wt % to 15 wt %. This embodiment may comprise an oil in water aggregate, such as a hydrophilic mixed non-ionic surfactant aggregate, which may comprise an oil in water microemulsion, a micellar solution or a cosolution.

The non-ionic surfactant system may be present in the aggregate in the range of 0.1 wt % to 80 wt %, preferably 0.2 wt % to 60 wt %, more preferably 0.2 wt % to 40 wt %.

The mass fraction of any given surfactant in a mixture of surfactants can vary within the range 0.01 to 0.99 although typically it will be in the range 0.10 to 0.80 depending on the degree of complexity of both the water soluble ingredient and the surfactant system.

In the first embodiment which may comprise the water in oil aggregate, such as a lipophilic mixed non-ionic surfactant aggregate in the form of water in oil microemulsions, a micellar solution or a cosolution the surfactant system may be present in the non-ionic surfactant aggregate in an amount in the range of 10 wt % to 90 wt %, preferably 10 wt % to 60 wt % and more preferably 10 wt % to 40 wt %.

In the second embodiment which may comprise the hexagonal, lamella, cylindrical or spherical aggregate structures, the surfactant system may be present in the aggregate in an amount in the range of 10 wt % to 60 wt %, preferably 10 wt % to 40 wt % and more preferably 10 wt % to 30 wt %.

In the third embodiment which may comprise the oil in water aggregate, such as a hydrophilic mixed non-ionic surfactant aggregate in the form of an oil in water microemulsion, a micellar solution or a cosolution the surfactant system may be present in the non-ionic surfactant aggregate in an amount in the range of 0.2 wt % to 40 wt %, preferably 0.2 wt % to 35 wt %, more preferably 0.2 wt % to 25 wt %.

The water may be present in the non-ionic surfactant aggregate in amount in the range of 0.1 wt % to 99.5 wt %, preferably 5 wt % to 99.5 wt %, more preferably 10 wt % to 99.5 wt %.

In the first embodiment, which may comprise a water in oil aggregate, such as a lipophilic non-ionic surfactant aggregate in the form of a water in oil microemulsion, a micellar solution or a cosolution the water may be present in the non-ionic surfactant aggregate in an amount 0.1 wt % to 35 wt %, preferably 5 wt % to 35 wt %, more preferably 10 wt % to 35 wt %.

In the second embodiment, which may comprise hexagonal, lamella, cylindrical or spherical aggregate structures, the water may be present in an amount in the range of 20 wt % to 55 wt %, preferably 30 wt % to 55 wt %, more preferably 35 wt % to 55 wt %.

In the third embodiment, which may comprise an oil in water aggregate, such as a hydrophilic non-ionic surfactant aggregate in the form of an oil in water microemulsion, a micellar solution or a cosolution the water may be present in the non-ionic surfactant aggregate in the range of 50 wt % to 99.5 wt %, preferably 55 wt % to 99.5 wt %, more preferably 60 wt % to 99.5 wt %.

The non-ionic surfactant aggregate may further comprise additives which may comprise one or more of the following: a synergist; a growth regulator, for example an insect growth regulator; a pH modifier; a wetting agent.

The synergist may be used with insecticides, such as synthetic pyrethroids, and may be in the form of an organic oil, such as piperonyl butoxide. Other types of oils may include natural oils such as canola oil, which may provide adjuvant effects when used in herbicidal formulations. The growth regulator may comprise a phenyl ether, such as pyriproxifen. The pH modifier may comprise an acid or an alkali which may be inorganic acids or inorganic alkalis. The pH modifier may be hydrochloric acid. Other suitable pH modifiers may comprise an amine such as triethanolamine. The wetting agent may comprise additional surfactants, which may comprise cationic, anionic, non-ionic or amphoteric substances. An example of a suitable wetting is an alkyl aryl sulphonate such as Nansa SSA, and/or a quaternary ammonium, such as Surfac DDAC. The wetting agents have the advantage of enhancing the wetting, spreading, or sticking of spray applications on target substrates.

Under the correct conditions, as would be appreciated by persons skilled in the art, at least one of the preferred embodiments form non-ionic surfactant aggregate structures, which may be lipophilic, and which can solubilise high concentrations of water insoluble organic compounds such as biocide active ingredients.

By selecting and balancing the surfactant chemistry correctly, as would be appreciated by persons skilled in the art, the lipophilic mixed non-ionic surfactant aggregates can take the form of discrete water in oil microemulsion droplets. The formation of such discrete droplets allow for the incorporation of significant quantities of water in liquid formulations contained in packaging members such as sachets formed from water soluble films such as polyvinylacohol (PVA).

According to another aspect of this invention, there is provided a packaged product comprising a water soluble packaging member containing a non-ionic aggregate as described above.

The water soluble packaging member may comprise a sealed sachet. The water soluble packaging member may be formed of a water soluble plastics material such as polyvinylalcohol (PVA).

Embodiments of the invention will now be described by way of example only.

A first embodiment of this invention comprises lipophilic mixed non-ionic surfactant aggregate which may be in the form of a water in oil microemulsion, a micellar solution or a cosolution. The non-ionic water in oil aggregate comprises a water insoluble active ingredient, such as an organic biocide. A suitable such biocide is a pesticide. The organic biocide is present in the water in oil aggregate in an amount in the range of 2 wt % to 40 wt %.

The water in oil aggregate further includes a surfactant system comprising at least first and second non-ionic surfactants to solubilise the biocide. The first non-ionic surfactant comprises at least one water soluble primary surfactant. The second non-ionic surfactant comprises at least one water insoluble cosurfactant. The first non-ionic surfactant has a high hydrophilic-lipophilic balance (HLB) relative to the second non-ionic surfactant, which has a relatively low HLB.

The surfactant system is present in the mixed non-ionic surfactant aggregate in an amount in the range 10 wt % to 90 wt % where the cosurfactant mass fraction, $(Pcos)m$, is in the range of 0.07 to 0.787. The mass fraction, $(Psurf)m$, for any individual non-ionic surfactant is of the order of 0.04-0.9. Water is also present in an amount in the range 0.1 wt % to 35 wt %. The system may also include other additives which do not contribute to the formation of the mixed non-ionic surfactant aggregates themselves, but which can provide enhanced properties. The other additives may be present in an amount in the range of 0.1 wt % to 20 wt %. These additives could include wetting agents, synergists, pH modifiers etc. The mixed non-ionic surfactant aggregates can be formed by any suitable method known in the art and such methods will immediately be known to persons skilled in the art on reading this specification. Specific examples of lipophilic mixed non-ionic surfactant aggregates which may be in the form of water in oil microemulsion droplets, a micellar solution or a cosolution are as follows:

Example 1: Oil External Pesticide Concentrate
$[Pact]_m = 0.237$, $[Psurf]_m = 0.763$, $[Pcos]_m = 0.07$

| Component | wt % |
|---|---|
| Alpha-cypermethrin (synthetic pyrethroid insecticide) | 5 |
| Tetramethrin (synthetic pyrethroid insecticide) | 5 |
| Piperonyl Butoxide (organic oil as synergist) | 10 |
| Pyriproxifen (phenyl ether insect growth regulator) | 2 |
| Neodol 91-2.5 (alcohol ethoxylate cosurfactants, CP < 0° C.) | 5 |
| Neodol 91-5 (alcohol ethoxylate primary surfactant, CP = 35° C.) | 46 |
| Pluronic PE10400 (EO-PO copolymer primary surfactant, CP = 75° C.) | 20 |
| Hydrochloric Acid, 28% (pH modifier) | 0.2 |
| Water | 6.8 |

Example 2: Oil External Pesticide Concentrate
$[Pact]_m = 0.182$, $[Psurf]_m = 0.818$, $[Pcos]_m = 0.565$

| Component | wt % |
|---|---|
| Permethrin (synthetic pyrethroid insecticide) | 2.5 |
| Propiconazole (triazole fungicide) | 11.25 |
| Surfac UN90 (alcohol ethoxylate primary surfactant, CP = 82° C.) | 27 |
| Pluronic PE10100 (EO-PO copolymer cosurfactant, CP~10° C. | 35 |
| Water | 24.25 |

Example 3: Oil External Pesticide Concentrate
$[Pact]_m = 0.143$, $[Psurf]_m = 0.857$, $[Pcos]_m = 0.5$

| Component | wt % |
|---|---|
| Permethrin (synthetic pyrethroid insecticide) | 10 |
| Neodol 91-5 (alcohol ethoxylate primary surfactant, CP = 35° C.) | 30 |
| Pluronic PE10100 (EG-PO copolymer cosurfactant CP~10° C.) | 30 |
| Water | 30 |

Example 4: Oil External Pesticide Concentrate
$[Pact]_m = 0.093$, $[Psurf]_m = 0.907$, $[Pcos]_m = 0.582$

| Component | wt % |
|---|---|
| IPBC (carbamate fungicide) | 7.5 |
| Neodol 91-2.5 (alcohol ethoxylate cosurfactant, CP < 0° C.) | 20 |
| Pluronic PE10100 (EO-PO copolymer cosurfactant, CP~10° C.) | 22.5 |
| Surfac UN90 (alcohol ethoxylate primary surfactant, CP = 82° C.) | 30.5 |
| Water | 19.5 |

Example 5: Oil External Pesticide Concentrate
$[Pact]_m = 0.04$, $[Psurf]_m = 0.96$, $[Pcos]_m = 0.381$

| Component | wt % |
|---|---|
| Bifenthrin (synthetic pyrethroid insecticide) | 3.16 |
| Neodol 91-5 (alcohol ethoxylate primary surfactants, CP = 35° C.) | 46.6 |
| Pluronic PE10100 (EO-PO copolymer cosurfactant, CP~10° C.) | 28.74 |
| Water | 21.5 |

Example 6: Oil External Pesticide Concentrate
$[Pact]_m = 0.345$, $[Purf]_m = 0.655$, $[Pcos]_m = 0.787$

| Component | wt % |
|---|---|
| IPBC (carbamate fungicide) | 15 |
| Propiconazole (triazole fungicide) | 15.1 |
| Pluronic PE10100 (EO-PO copolymer cosurfactant, CP~10° C.) | 26.88 |
| Neodol 91-2.5 (alcohol ethoxylate cosurfactant, CP < 0° C.) | 18 |
| Neodol 91-5 (alcohol ethoxylate primary surfactant, CP = 35° C.) | 12.15 |
| Hydrochloric Acid, 28% (pH modifier) | 0.2 |
| Fluorad FC171 (fluorinated alkyl alkoxylate wetting agent | 0.1 |
| Water | 12.57 |

Example 7: Oil External Pesticide Concentrate
$[Pact]_m = 0.344$, $[Psurf]_m = 0.656$, $[Pcos]_m = 0.071$

| Component | wt % |
|---|---|
| IPBC (carbamate fungicide) | 15 |
| Propiconazole (triazole fungicide) | 15.1 |
| Flufenoxuron (Benzoylurea insect growth regulator) | 1.1 |
| Alkamuls 719E (castor oil ethoxylate primary surfactant, CP > 100° C.) | 50.5 |
| Surfac UN90 (alcohol ethoxylate primary surfactant, CP = 82° C.) | 4.7 |
| Neodol 91-2.5 (alcohol ethoxylate cosurfactant, CP < 0° C.) | 4.2 |
| Surfac DDAC (quarternary ammonium wetting agent) | 1.5 |
| Hydrochloric Acid, 28% (pH modifier) | 0.1 |
| Water | 7.8 |

Example 8: Oil External Pesticide Concentrate
$[Pact]_m = 0.358$, $[Psurf]_m = 0.642$, $[Pcos]_m = 0.226$

| Component | wt % |
|---|---|
| Alpa-cypermethrin (synthetic pyrethroid insecticide) | 5 |
| Tetramethrin (synthetic pyrethroid insecticide) | 5 |
| Piperonyl Butoxide (organic oil as synergist) | 20 |
| Pyriproxifen (phenyl ether insect growth regulator) | 2 |
| Neodol 91-2.5 (alcohol ethoxylate cosurfactant, CP < 0° C.) | 13 |
| Emulan EL40 (castor oil ethoxylate primary surfactant, CP > 100° C.) | 44.5 |
| Nansa SSA (alkyl aryl sulphonic acid pH modifier) | 0.25 |
| Water | 10.25 |

Example 9: Oil External Pesticide Concentrate
$[Pact]_m = 0.105$, $[Psurf]_m = 0.895$, $[Pcos]_m = 0.385$

| Component | wt % |
|---|---|
| Bifenthrin (synthetic pyrethroid insecticide) | 8.43 |
| Lutensol XL70 (alcohol ethoxylate primary surfactant, CP~60° C.) | 44 |

Example 9: Oil External Pesticide Concentrate
$[Pact]_m = 0.105$, $[Psurf]_m = 0.895$, $[Pcos]_m = 0.385$

| Component | wt % |
|---|---|
| Pluronic PE10100 (EO-PO copolymer cosurfactant, CP~10° C.) | 27.57 |
| Water | 20 |

Example 10: Oil External Pesticide Concentrate
$[Pact]_m = 0.303$, $[Psurf]_m = 0.697$, $[Pcos]_m = 0.351$

| Component | wt % |
|---|---|
| Bifenthrin (synthetic pyrethroid insecticide) | 26.32 |
| Neodol 91-5 (alcohol ethoxylate primary surfactant, CP = 35° C.) | 38.11 |
| Pluronic PE10100 (EO-PO copolymer cosurfactant, CP~10° C.) | 20.57 |
| Water | 13 |

Example 11: Oil External Pesticide Concentrate
$[Pact]_m = 0.141$, $[Psurf]_m = 0.859$, $[Pcos]_m = 0.5$

| Component | wt % |
|---|---|
| Zeta-cypermethrin (synthetic pyrethroid insecticide) | 11.5 |
| Neodol 91-5 (alcohol ethoxylate primary surfactant, CP~10° C.) | 35 |
| Pluronic PE10100 (EO-PO copolymer cosurfactant, CP~10° C.) | 35 |
| Nansa SSA (alkyl aryl sulphonic acid pH modifier) | 0.2 |
| Water | 18.3 |

Example 12: Oil External Pesticide Concentrate
$[Pact]_m = 0.125$, $[Psurf]_m = 0.875$, $[Pcos]_m = 0.25$

| Component | wt % |
|---|---|
| Bifenthrin (synthetic pyrethroid insecticide) | 5.25 |
| Flonicamid (pyridinecarboxamide insecticide) | 5.05 |
| Neodol 91-5 (alcohol ethoxylate primary surfactant, CP = 35° C.) | 27 |
| Pluronic PE10100 (EO-PO copolymer cosurfactant, CP~10° C.) | 18 |
| Emulan EL40 (castor oil ethoxylate primary surfactant, CP > 100° C.) | 27 |
| Water | 17.7 |

Example 13: Oil External Pesticide Concentrate
$[Pact]_m = 0.23$, $[Psurf]_m = 0.77$, $[Pcos]_m = 0.341$

| Component | wt % |
|---|---|
| Carfentrazone ethyl (triazolone herbicide) | 13.3 |
| Canola Oil (vegetable oil adjuvant) | 6 |
| Surfac UN90 (alcohol ethoxylate primary surfactant, CP = 82° C.) | 17 |
| Neodol 91-2.5 (alcohol ethoxy late cosurfactant, CP < 0° C.) | 22 |
| Emulan EL40 (castor oil ethoxylate primary surfactant, CP > 100° C.) | 25.5 |
| Water | 16.2 |

Example 14: Oil External Pesticide Concentrate
$[Pact]_m = 0.431$, $[Psurf]_m = 0.569$, $[Pcos]_m = 0.267$

| Component | wt % |
|---|---|
| Carfentrazone ethyl (triazolone herbicide) | 22.1 |
| Canola Oil (vegetable oil adjuvant) | 12 |
| Neodol 91-2.5 (alcohol ethoxylate cosurfactant, CP < 0° C.) | 12 |
| Emulan EL40 (castor oil ethoxylate primary surfactant, CP > 100° C.) | 33 |
| Water | 20.9 |

The term "EO-PO copolymer" means an ethylene oxide-propylene oxide copolymer."

The formation of discrete water in oil microemulsion droplets can be demonstrated experimentally by following the conductivity during water enrichment of systems containing a hydrocarbon (e.g. pesticide ai) and two surfactants. In Tables 2 and 3 the conductivity as a function of the water mass fraction, $[Paq]m$, given by:

$$[Paq]m = \text{mass of water/total mass of system}$$

is compared for two systems in which the only difference is the cosurfactant mass fraction, $(Pcos)m$, given by:

$$[Pcos]m = \text{mass of cosurfactant/total surfactant mass}$$

TABLE 2

Conductivity vs [Paq]m at [Pcos]m 0.575

| (Paq)m | Conductivity (mu · S) |
|---|---|
| 0 | 0 |
| 0.025 | 11 |
| 0.05 | 17 |
| 0.065 | 33 |
| 0.09 | 67 |
| 0.11 | 100 |
| 0.15 | 210 |
| 0.2 | 535 |
| 0.25 | 2000 |
| 0.27 | 3200 |
| 0.3 | 5330 |

TABLE 3

Conductivity vs [Paq]m at [Pcos]m 0.575

| (Paq)m | Conductivity (mu · S) |
|---|---|
| 0. | 0 |
| 0.01 | 1 |
| 0.025 | 4 |
| 0.05 | 8 |
| 0.06 | 12 |
| 0.07 | 14 |
| 0.09 | 13.5 |
| 0.10 | 13 |
| 0.13 | 8 |
| 0.15 | 7 |
| 0.175 | 5 |
| 0.20 | 4 |
| 0.225 | 3 |
| 0.25 | 2.5 |
| 0.30 | 2.5 |
| 0.32 | 80 |
| 0.34 | 400 |
| 0.35 | 550 |

At [Pcos]m 0.575 as [Paq]m increases conductivity increase dramatically showing percolative behaviour. This type of system is best described as being due to the presence of either a bicontinuous (cosolubilised) system or aggregation units with very flexible interfaces and short life times.

At (Pcos)m 0.65 the conductivity remains very low and varies in a non-monotonous manner as [Paq]m increases. Initially there is an increase in conductivity as water is added due to the formation of hydrated surfactant aggregates. At some point, (Paq)m 0.06 to 0.1, conductivity begins to decrease as more water is added due to the replacement of hydrated surfactant aggregates with water in oil microemulsion droplets having definite water cores. As more water is added conductivity remains more or less constant as more and more discrete droplets are formed until a further critical point is reached at (Paq)m 0.3-0.32 where conductivity begins to increase rapidly as more water is added. This change is brought about by either a change from spherical to non-spherical droplets or an aggregation of water droplets or indeed a degree of phase inversion brought about by the increase in the mass fraction of dispersed (water) phase.

The above examples of the invention can be packed into standard plastic bottles made from materials such as heavy density polyethylene (HDPE) plastics. Alternatively, in some case, where the water is encapsulated within the mixed surfactant aggregate, thereby preventing contact between the water and the water soluble film, they can be incorporated into water soluble sachets made from materials such as PVA.

The above embodiments are concentrates in the form of lipophilic mixed non-ionic surfactant aggregates which are thermodynamically stable and contain high levels of active ingredient. They are intended for dilution in water whereupon the aggregates spontaneously invert to thermodynamically stable hydrophilic mixed non-ionic surfactant aggregates which can be in the form of oil in water microemulsions, micellar solutions etc. These diluted systems can then be used in a variety of applications.

The stability of these diluted concentrates is best shown by the following examples where dilutions were prepared in waters of various degrees of hardness (expressed as ppm calcium carbonate) and the turbidity measured as a function of time and temperature using an Orbeco-Hellige Digital Turbidimeter.

TABLE 4

Turbidity vs Water Hardness @ RT
(Example 3 above diluted @ 1 in 200)

| Water Hardness | Turbidity vs Time | | |
|---|---|---|---|
| | Initial | 4 hours | 24 hours |
| 0 ppm | 12.8 | 11.6 | 13.1 |
| 100 ppm | 13.6 | 11.4 | 12 |
| 342 ppm | 14 | 11.9 | 12.4 |
| 500 ppm | 13 | 11.8 | 12 |

TABLE 5

Turbidity (24 hours) vs Water Hardness vs Temperature
(Example 5 above diluted @ 1 in 12.5)

| Water Hardness | Turbidity vs Temperature | | |
|---|---|---|---|
| | Initial 4° C. | 4 hours RT | 24 hours 35° C. |
| 0 ppm | 2 | 2.6 | 4.9 |
| 100 ppm | 2 | 2.8 | 4.7 |
| 342 ppm | 1.8 | 2.7 | 4.6 |
| 500 ppm | 1.9 | 2.6 | 4.8 |

These can be compared to results obtained with a similar system based on a combination of an anionic surfactant and a non-ionic surfactant as given below:

| Component | wt % |
|---|---|
| Propiconazole (triazole fungicide) | 5.63 |
| Solvesso 150 (naphthenic hydrocarbon solvent) | 4.61 |
| Nansa SSA (dodecyl benzene sulphonic acid - anionic surfactant) | 7.14 |
| Pluronic PE10100 (EO-PO block copolymer surfactant) | 9.72 |
| Sodium Hydroxide | 0.25 |
| Water | 72.65 |

The turbidity of dilutions at 1 in 12.5 were prepared in a range of hard waters and measured as a function of time at RT, the results are given in Table 6 below:

TABLE 6

Turbidity (24 hours) vs Water Hardness vs Temperature
(Anionic - Non-ionic surfactant combination)

| Water Hardness | Turbidity vs Temperature | | |
|---|---|---|---|
| | Initial | 4 hours | 24 hours |
| 0 ppm | 0.7 | 1.1 | 0.8 |
| 100 ppm | 60.7 | 163.0* | 195.0* |
| 342 ppm | 240.0 | 263.0* | 282.0* |
| 500 ppm | 281.0 | 310.0* | 505.0* |

Note:
*these samples showed signs of sedimentation upon standing.

Another technique which can be used to look at effects such as water hardness on the diluted systems is that of Photo Correlation Spectroscopy which uses light scattering as a means of determining particle size. Particles suspended in a medium such as water are subjected to random Brownian Diffusion such that small particles will move much faster than larger ones. The rate of diffusion can be measured by examining the change in intensity of laser light that is scattered at 90° and the radius of the particles, Rh, is given by the equation:

$$Rh = kT/6\pi\eta nD$$

where
k=Boltzmann's constant
T=absolute temperature
$\eta$=viscosity of the fluid medium
D=diffusion constant
Using this technique samples were prepared and the particle size determined as a function of water hardness and temperature, results are shown in tables 7 and 8 below:

TABLE 7

Particle Size (nm) vs Water Hardness @ RT
(Example 3 above @ 1 in 200 dilution)

| Water Hardness | Particle Diameter (nm) | |
|---|---|---|
| | Initial | 24 hours |
| 0 ppm | 23.6 | 22 |
| 100 ppm | 23.4 | 22.3 |
| 342 ppm | 22.4 | 21.9 |
| 500 ppm | 22.1 | 23.5 |

These dilutions showed a very small degree of translucency indicative of oil in water systems which are in the form of microemulsions and this is confirmed by a typical particle size in the range of 10 to 100 nm.

TABLE 8

Particle Size (24 hours) vs Water Hardness vs Temperature
(Example 5 above @ 1 in 25 dilution)

| Water Hardness | Particle Diameter (nm) | | | |
|---|---|---|---|---|
| | 25° C. | 30° C. | 40° C. | 45° C. |
| 0 ppm | | 12.1 | | |
| 100 ppm | | 10.4 | | |
| 342 ppm | | 10.8 | | |
| 500 ppm | 11.7 | 11.3 | 14.2 | 15.2 |

All of these samples have the appearance of "water" as confirmed by the turbidity readings, the particle size distribution includes a significant number of particles with diameters below 10 nm and they are probably best described as micellar solutions.

A second embodiment of this invention comprises liquid crystalline "gels" having for example hexagonal, lamella, cylindrical or spherical aggregate structures which will contain water insoluble organic biocide(s) which may be a pesticide active ingredient. The biocide(s) will be present in these structures in an amount in the range 0.1 wt % to 35.0 wt %. The surfactant system will comprise a mixture of at least two non-ionic surfactant molecules with a total surfactant concentration in the range 10.0 wt % to 60.0 wt % with the cosurfactant mass fraction, $[Pcos]m$, of the order 0.04 to 0.65. Water will also be present in these structures at a concentration in the range 20.0 wt % to 55.0 wt %. The system may also include other additives which do not contribute to the formation of the mixed non-ionic surfactant aggregate, themselves, but can provide enhanced properties and which may be present in an amount in the range 0.1 wt % to 20 wt %. These other additives may include wetting agents, synergists, pH modifiers etc.

The mixed non-ionic surfactant aggregates can be formed by any suitable method known in the art and such methods will immediately be known to persons skilled in the art on reading this specification. Specific examples of these liquid crystalline "gels" are as follows:

Example 15: Pesticide Gel
$[Pact]_m = 0.041$, $[Psurf]_m = 0.959$, $[Pcos]_m = 0.636$

| Component | wt % |
|---|---|
| IPBC (carbamate fungicide) | 2.13 |
| Lutensol TO 8 (alcohol ethoxylate primary surfactant, CP = 60° C.) | 18.31 |
| Pluronic PE8100 (EO-PO copolymer cosurfactant, CP~15° C.) | 32.06 |
| Water | 47.5 |

Example 16: Pesticide Gel
$[Pact]_m = 0.043$, $[Psurf]_m = 0.957$, $[Pcos]_m = 0.636$

| Component | wt % |
|---|---|
| Permethrin (synthetic pyrethroid insecticide) | 0.5 |
| Propiconazole (triazole fungicide) | 2 |
| Lutensol ON 70 (alcohol ethoxylate primary surfactant, CR~60° C.) | 20 |

Example 16: Pesticide Gel
$[Pact]_m = 0.043$, $[Psurf]_m = 0.957$, $[Pcos]_m = 0.636$

| Component | wt % |
|---|---|
| Pluronic PE10100 (EO-PO copolymer cosurfactant, CP~10° C.) | 35 |
| Aerosol OT100 (di-octyl sulphsuccinate wetting agent) | 0.15 |
| Water | 42.35 |

Example 17: Pesticide Gel

| Component | wt % |
|---|---|
| Flufenoxuron (Benzoylurea insect growth regulator) | 0.1 |
| Lutensol AO7 (alcohol ethoxylate primary surfactant, CP = 43° C.) | 18.5 |
| Pluronic PE10100 (EO-PO copolymer cosurfactant, CP~10° C.) | 20 |
| Pluronic PE10400 (EO-PO copolymer primary surfactant, CP = 75° C.) | 10.5 |
| Fluorad FC171 (Fluorinated alkyl alkoxylated wetting agent) | 0.1 |
| Water | 50.8 |

These types of system are intended for use without dilution and can supply high active ingredient loadings at highly targeted areas. They have significant potential in the treatment of large dimensional structural timbers where they can be injected into pre-drilled holes providing very good active ingredient distribution throughout the timber which is not possible using conventional spray or brush applications to exposed surfaces.

The viscosity of these "gels" thus formed by these mixed non-ionic surfactant blends can vary significantly in the range of 1000 cPs to >100,000 cPs and will depend to a large extend on the ratio of the various non-ionic surfactants.

If the cosurfactant mass fraction, ($[Pcos]m$ is high (>0.3) medium viscosity "gels" corresponding to an hexagonal array of aggregates tend to form adjacent to the region of lipophilic mixed surfactant aggregates. If this mass fraction is low (<0.2) high viscosity "gels" corresponding to a lamella structures tend to form adjacent to the region of hydrophilic mixed surfactant aggregates.

The flow properties of both types of "gel" are best described by pseudoplastic behaviour. When injected into 1 cm pre-drilled holes in timber the mass uptake of these "gels" appears to be quite significant with movement of the active ingredient in some cases exceeding 20 cm. Moreover, analytical studies indicate that diffusion of the "gel" through the timber occurs without phase separation.

A third embodiment of this invention comprises hydrophilic mixed non-ionic surfactant aggregates, which may be in the form of micellar solutions or oil in water microemulsions, which contain water insoluble organic biocide(s) which may be a pesticide active ingredient.

The organic biocide(s) will be present in these aggregates in an amount in the range 0.001 wt % to 20 wt %. The surfactant system comprises at least one water soluble primary surfactant, and at least one water insoluble cosurfactant with the total surfactant concentration being in the range of 0.2 wt % to 40 wt %. The mass fraction of the cosurfactant $[Pcos]m$ is of the order of 0.17-0.47. Water will also be present in the aggregate in an amount in the range 50 wt % to 99.5 wt %. The system may also include other additives which do not contribute to the formation of the mixed non-ionic surfactant aggregates themselves, but which can provide enhanced properties. These other may be present in an amount in the range 0.1 wt % to 20 wt %, these may include wetting agents, synergists, pH modifiers etc.

The mixed non-ionic surfactant aggregates can be formed by any suitable method known in the art and such methods will immediately be known to persons skilled in the art on reading this specification. Specific examples of hydrophilic mixed non-ionic surfactant aggregates are as follows:

Example 18: Water External Pesticide Concentrate
$[Pact]_m = 0.048$, $[Psurf]_m = 0.952$, $[Pcos]_m = 0.333$

| Component | wt % |
|---|---|
| Bifenthrin (synthetic pyrethroid insecticide) | 0.3 |
| Neodol 91-5 (alcohol ethoxylate primary surfactant, CP = 35° C.) | 4 |
| Pluronic PE10100 (EO-PO copolymer cosurfactant, CP~10° C.) | 2 |
| Water | 93.7 |

Example 19: Water External Pesticide Concentrate
$[Pact]_m = 0.068$, $[Psurf]_m = 0.932$, $[Pcos]_m = 0.421$

| Component | wt % |
|---|---|
| Bifenthrin (synthetic pyrethroid insecticide) | 8.43 |
| Neodol 91-5 (alcohol ethoxylate primary surfactant, CP = 35° C.) | 24 |
| Pluronic PE10100 (EO-PO copolymer cosurfactant, CR~10° C.) | 17.57 |
| Water | 50 |

Example 20: Water External Pesticide Concentrate
$[Pact]_m = 0.169$, $[Psurf]_m = 0.831$, $[Pcos]_m = 0.423$

| Component | wt % |
|---|---|
| Bifenthrin (synthetic pyrethroid insecticide) | 2.1 |
| Neodol 91-5 (alcohol ethoxylate primary surfactant, CP = 35° C.) | 16.74 |
| Pluronic PE10100 (EO-PO copolymer cosurfactant, CP~10° C.) | 12.16 |
| Water | 69 |

Example 21: Water External Pesticide Concentrate
$[Pact]_m = 0.067$, $[Psurf]_m = 0.933$, $[Pcos]_m = 0.214$

| Component | wt % |
|---|---|
| Zeta-cypermethrin (synthetic pyrethroid insecticide) | 2.5 |
| Neodol 91-5 (alcohol ethoxylate primary surfactant, CP = 35° C.) | 17.5 |
| Pluronic PE10100 (EO-PO copolymer cosurfactant, CP~10° C.) | 7.5 |
| Emulan EL40 (castor oil ethoxylate primary surfactant, CP > 100° C.) | 10 |
| Nansa SSA (alkyl aryl sulphonic acid pH modifier) | 0.2 |
| Water | 62.3 |

Example 22: Water External Pesticide Concentrate
$[Pact]_m = 0.256$, $[Psurf]_m = 0.744$, $[Pcos]_m = 0.172$

| Component | wt % |
|---|---|
| Carfentrazone-ethyl (triazolone herbicide) | 5 |
| Canola Oil (vegetable oil adjuvant) | 5 |
| Neodol 91-2.5 (alcohol ethoxylate cosurfactant, CP < 0° C.) | 5 |
| Lutensol XL70 (alcohol ethoxylate primary surfactant, CP~60° C.) | 4 |
| Emufan EL40 (castor oil ethoxylate primary surfactant, CP > 100° C.) | 20 |
| Water | 61 |

Example 23: Water External Pesticide Concentrate
$[Pact]_m = 0.185$, $[Psurf]_m = 0.815$, $[Pcos]_m = 0.273$

| Component | wt % |
|---|---|
| Bifenthrin (synthetic pyrethroid insecticide) | 1.25 |
| Flonicamid (pyridinecarboxamide insecticide) | 1.25 |
| Piperonyl Butoxide (organic oil as synergist) | 5 |
| Neodol 91-5 (alcohol ethoxylate primary surfactant, CP = 35° C.) | 12 |
| Pluronic PE10100 (EO-PO copolymer cosurfactant, CP~10° C.) | 9 |
| Emulan EL40 (castor oil ethoxylate primary surfactant, CP > 100° C.) | 12 |
| Aerosol OT100 (di-octyl sulphosuccinate wetting agent) | 0.5 |
| Water | 59 |

Example 24: Water External Pesticide Concentrate
$[Pact]_m = 0.185$, $[Psurf]_m = 0.815$, $[Pcos]_m = 0.475$

| Component | wt % |
|---|---|
| Permethrin (synthetic pyrethroid insecticide) | 5 |
| Neodol 91-5 (alcohol ethoxylate primary surfactant, CP = 35° C.) | 13 |
| Pluronic PE10100 (EO-PO copolymer cosurfactant, CP~10° C.) | 14.5 |
| Water | 67.5 |

Example 25: Water External Pesticide Concentrate
$[Pact]_m = 0.197$, $[Psurf]_m = 0.803$, $[Pcos]_m = 0.425$

| Component | wt % |
|---|---|
| Propiconazole (triazole fungicide) | 2.82 |
| IPBC (carbamate fungicide) | 2.82 |
| Permethrin (synthetic pyrethroid insecticide) | 1.25 |
| Neodol 91-5 (alcohol ethoxylate primary surfactant, CP = 35° C.) | 16.17 |
| Pluronic PE8100 (EO-PO copolymer cosurfactant, CP~15° C.) | 11.95 |
| Fluorad FC171 (fluorinated alkyl alkoxylate wetting agent) | 0.2 |
| Water | 64.79 |

Example 26: Water External Pesticide Concentrate
$[Pact]_m = 0.158$, $[Psurf]_m = 0.842$, $[Pcos]_m = 0.25$

| Component | wt % |
|---|---|
| Propiconazole (triazole fungicide) | 5.63 |
| Neodol 91-2.5 (alcohol ethoxylate cosurfactant, CP < 0° C.) | 7.5 |
| Lutensol XL90 (alcohol ethoxylate primary surfactant, CP~90° C.) | 22.5 |
| Water | 64.37 |

The specific examples above (18 to 26) are all comprised of hydrophilic mixed non-ionic surfactant aggregates which may be in the form of cosolubilised systems, micellar solutions or oil in water microemulsions. They are all thermodynamically stable and are designed for further dilution with water prior to application for a range of uses and moreover upon further dilution in water the systems maintain their thermodynamic stability.

Given that the external phase of these systems is in all cases water they are not suitable for incorporation into sachets made from water soluble PVA films and would be generally supplied as concentrates in conventional plastic (HDPE) containers.

The stability of both the concentrates and dilutions can be studied by techniques already described above for the study of oil external pesticide concentrates.

The preferred embodiments of the non-ionic surfactant aggregates can be considered as being comprised of three main components, as follows:
(a) an active ingredient phase which comprises the biocidal active ingredient plus any synergists, adjuvants etc;
(b) a surfactant phase which comprises at least one non-ionic surfactant which is soluble in water (having an aqueous Cloud Point>25° C. and designated as the "primary surfactant") and at least one non-ionic surfactant which is insoluble in water (having an aqueous Cloud Point<25° C. and designated as the "cosurfactant") where the Cloud Point is determined by any suitable method such as the German standard method (DIN 53917); and
(c) an aqueous phase which comprises water and any additives such as pH modifiers, wetting agents, preservatives, colourants etc.

The active ingredient phase and the surfactant phase collectively can be considered as the organic phase.

The formation and stabilisation of these mixed non-ionic surfactant aggregates, which can be in the form of:
(a) a lipophilic surfactant aggregate which is in the form of a concentrated active ingredient composition which of itself is thermodynamically stable and is diluted with water prior to use to spontaneously form thermodynamically stable hydrophilic surfactant aggregates which can be in the form of microemulsions, micellar solutions etc.;
(b) a hydrophilic surfactant aggregate which is in the form of a concentrated active ingredient composition which of itself is thermodynamically stable and is diluted with water prior to use whilst retaining the thermodynamically stability of the aggregates which can be in the form of microemulsions, micellar solutions etc.; and
(c) a hydrophilic surfactant aggregate which is in the form of a thermodynamically stable Ready to Use (RtU) active ingredient composition.

is governed by the relationship between the various three component phases defined above.

The key relationships can be defined by the mass fraction ratio of the various phases where the key mass fraction ratios are:
(a) active ingredient mass fraction [Pact]m, given by

[$P$act]$m$=mass of active ingredient phase/mass of organic phase (b) total surfactant mass fraction, [Psurf]m, given by:

[$P$surf]$m$=mass of non-ionic surfactants/mass of organic phase (c) cosurfactant mass fraction, [Pcos]m, given by:

[$P$cos]$m$=mass of cosurfactant(s)/mass of non-ionic surfactants.

Whilst all three mass fractions will exert an influence on the formation and stabilisation of thermodynamically stable, single phase surfactant aggregates it is [Pcos]m, the cosurfactant mass fraction which is the overriding driver for this process.

Combinations of water soluble primary surfactant(s) with water insoluble cosurfactant(s) can be varied in order to change the overall hydrophilic-lipophilic nature of the surfactant blend. The optimum stability of the aggregate system is achieved when [Pcos[m matches as closely as possible the Required Hydrophilic Lipophilic Balance (Required HLB) of the active ingredient phase.

The Required HLB of the active ingredient phase will be dependent of the surfactant system used. Consider the above examples 1 and 8 below where the active ingredient phase is a mixture of four components, alpha-cypermethrin, tetramethrin, piperonyl butoxide and pyriproxifen. To determine the Required HLB we need to calculate the Contribution to HLB, (Con-HLB), for each surfactant by multiplying an individual surfactant mass fraction, [Psurf-I]m, by the actual HLB of that surfactant, where:

[$P$surf-$I$]$_m$=mass of individual non-ionic surfactant/ total mass of non-ionic surfactants and the Required HLB is the sum of all the Con-HLB values.

| Example 1 | | | |
|---|---|---|---|
| Surfactant/type | HLB | [Psurf-I]$_m$ | Con-HLB |
| Neodol 91-2.5/cosurfactant | 8.1 | 5.0/71.0 | 0.57 |
| Neodol 91-5/prim.surfactant | 11.6 | 46.0/71.0 | 7.52 |
| Pluronic PE10400/prim.surfactant | 13.0 | 20.0/71.0 | 3.66 |
| Required HLB | | | 11.75 |

| Example 8 | | | |
|---|---|---|---|
| Surfactant/type | HLB | [Psurf-I]$_m$ | Con-HLB |
| Neodol 91-2.5/cosurfactant | 8.1 | 13.0/57.5 | 1.83 |
| Emulan EL40/prim.surfactant | 13.0 | 44.0/57.5 | 9.95 |
| Required HLB | | | 11.69 |

Consider now the above examples 13 and 14 below where the active ingredient phase is a mixture of two components, carfentrazone-ethyl and canola oil:

| Example 13 | | | |
|---|---|---|---|
| Surfactant/type | HLB | [Psur-I]$_m$ | Con-HLB |
| Neodol 91-2.5/cosurfactant | 8.1 | 22.0/64.5 | 2.76 |
| Surfac UN90/prim.surfactant | 13.7 | 17.0/64.5 | 3.61 |
| Emulan EL40/prim.surfactant | 13.0 | 25.5/64.5 | 5.14 |
| Required HLB | | | 11.51 |

Example 14

| Surfactant/type | HLB | $[Psurf\text{-}I]_m$ | Con-HLB |
|---|---|---|---|
| Neodol 91-2.5/cosurfactant | 8.1 | 12.0/45.0 | 2.16 |
| Emulan EL40/prim.surfactant | 13.0 | 33.0/45.0 | 9.53 |
| Required HLB | | | 11.78 |

Now consider the examples 20 and 12 below:

Example 20
The active ingredient phase comprises a single component, bifenthrin, which is an extremely lipophilic molecule and this is reflected in the much lower value for Required HLB:

| Surfactant/type | HLB | $[Psurf\text{-}I]_m$ | Con-HLB |
|---|---|---|---|
| Pluronic PE10100/cosurfactant | 1.0 | 17.57/41.57 | 0.42 |
| Neodol 91-5/prim.surfactant | 11.6 | 24.0/41.57 | 6.70 |
| Required HLB | | | 7.12 |

Example 12
Here we have a 50:50 mixture of bifenthrin and flonicamid as the active ingredient phase where the flonicamid is considerably more hydrophilic in nature and the change in the nature of the active ingredient phase is reflected in the Required HLB.

| Surfactant/type | HLB | $[Psurf\text{-}I]_m$ | Con-HLB |
|---|---|---|---|
| Pluronic PE10100 | 1.0 | 18.0/72.0 | 0.25 |
| Neodol 91-5/prim.surfactant | 11.6 | 27.0/72.0 | 4.35 |
| Emulan EL40/prim.surfactant | 11.6 | 27.0/72.0 | 4.86 |
| Required HLB | | | 9.46 |

As an alternative these hydrophilic mixed non-ionic surfactant aggregates can be used in the preparation of Ready to use (Rtu), pesticide formulations with specific examples as follows:

Example 27: Water External Pesticide Rtu
$[Pact]_m = 0.034$, $[Psurf]_m = 0.966$, $[Pcos]_m = 0.167$

| Component | wt % |
|---|---|
| Bifenthrin (synthetic pyrethroid insecticide) | 0.003 |
| Flonicamid (pyridinecarboxamide insecticide) | 0.003 |
| Piperonyl Butoxide (organic oil as synergist) | 0.015 |
| Neodol 91-5 (alcohol ethoxylate primary surfactant, CP = 35° C.) | 0.4 |
| Pluronic PE10100 (EO-PO copolymer cosurfactant, CP~10° C.) | 0.1 |
| Emulan EL40 (castor oil ethoxylate primary surfactant, CP > 100° C.) | 0.1 |
| Aerosol OT 100 (di-octyl sulphosuccinate wetting agent) | 0.1 |
| Water | 99.349 |

Example 28: Water External Pesticide Rtu
$[Pact]_m = 0.141$, $[Psurf]_m = 0.859$, $[Pcos]_m = 0.5$

| Component | wt % |
|---|---|
| Pyrethrum 25% (natural pyrethrins insecticide) | 0.02 |
| Piperonyl Butoxide (organic oil as synergist) | 0.22 |
| Myclobutanil (conazole fungicide) | 0.006 |
| Neodol 91-2.5 (alcohol ethoxylate cosurfactant, CP < 0° C.) | 0.75 |
| Surfac UN90 (alcohol ethoxylate primary surfactant, CP = 82° C.) | 0.25 |
| Emulan EL40 (castor oil ethoxylate primary surfactant, CP > 100° C.) | 0.5 |
| Water | 98.254 |

Example 29: Water External Pesticide Rtu
$[Pact]_m = 0.284$, $[Psurf]_m = 0.716$, $[Pcos]_m = 0.441$

| Component | wt % |
|---|---|
| Zeta-cypermethrin (synthetic pyrethroid insecticide) | 0.015 |
| Neodol 91-5 (alcohol ethoxylate primary surfactant, CP = 35° C.) | 0.4 |
| Pluronic PE10100 (EO-PO copolymer surfactant, CP~10° C.) | 0.1 |
| Emulan EL40 (castor oil ethoxylate primary surfactant, CP > 100° C.) | 0.1 |
| Nansa SSA (alkyl aryl sulphonic acid pH modifier) | 0.02 |
| Water | 99.365 |

Example 30: Water External Pesticide Rtu
$[Pact]_m = 0.284$, $[Psurf]_m = 0.716$, $[Pcos]_m = 0.441$

| Component | wt % |
|---|---|
| Natural pyrethrums, 25% (natural pyrethrin insecticide) | 1.2 |
| Piperonyl Butoxide (organic oil as synergist) | 1.5 |
| Neodol 91-2.5 (alcohol ethoxylate cosurfactant, CP < 0° C.) | 0.3 |
| Neodol 91-5 (alcohol ethoxylate primary surfactant, CP = 35° C.) | 3.8 |
| Pluronic PE10100 (EO-PO copolymer cosurfactant, CP~10° C.) | 2.7 |
| Water | 90.5 |

Example 31: Water External Pesticide Rtu
$[Pact]_m = 0.186$, $[Psurf]_m = 0.814$, $[Pcos]_m = 0.333$

| Component | wt % |
|---|---|
| Permethrin (synthetic pyrethroid insecticide) | 0.1 |
| Propiconazole (triazole fungicide) | 0.225 |
| IPBC (carbamate fungicide) | 0.225 |
| Neodol 91-2.5 (alcohol ethoxylate cosurfactant, CP < 0° C.) | 0.8 |
| Neodol 91-5 (alcohol ethoxylate primary surfactant CP = 35° C.) | 0.8 |
| Pluronic PE10400 (EO-PO copolymer primary surfactant CP = 75° C.) | 0.8 |
| Aerosol OT100 (di-octyl sulphosuccinate wetting agent) | 0.05 |
| Water | 97 |

Example 32: Water External Pesticide Rtu
$[Pact]_m = 0.006$, $[Psurf]_m = 0.994$, $[Pcos]_m = 0.3$

| Component | wt % |
|---|---|
| Bifenthrin (synthetic pyrethroid insecticide) | 0.003 |
| Neodol 91-5 (alcohol ethoxylate primary surfactant CP = 35° C.) | 0.35 |

-continued

Example 32: Water External Pesticide Rtu
$[Pact]_m = 0.006, [Psurf]_m = 0.994, [Pcos]_m = 0.3$

| Component | wt % |
|---|---|
| Pluronic PE10100 (EO-PO copolymer cosurfactant, CP~10° C.) | 0.15 |
| Water | 99.497 |

Example 33: Water External Pesticide Rtu

| Component | wt % |
|---|---|
| Permethrin (synthetic pyrethroid insecticide) | 0.2 |
| Neodol 91-2.5 (alcohol ethoxylate cosurfactant, CP < 0° C.) | 1.3 |
| Neodol 91-5 (alcohol ethoxylate primary surfactant, CP = 35° C.) | 2 |
| Neodol 91-8 (alcohol ethoxylate primary surfactant, CP = 82° C.) | 0.9 |
| Emulan EL40 (castor oil ethoxylate primary surfactant CP > 100° C.) | 1 |
| Water | 94.6 |

The formulations of examples 27 to 33 above are not designed for further dilution and they are thermodynamically stable hydrophilic mixed non-ionic surfactant aggregates which can be in the form of cosolubilised systems, micellar solutions or oil in water microemulsions. They are to be supplied in conventional plastic bottles made from HDPE or PET and would be expected to have stability allowing for a two year shelf-life under UK ambient conditions.

According to another aspect of this invention certain thermodynamic and physical properties, for example lack of phase separation, small particle size and low surface tension, of the hydrophilic mixed non-ionic surfactant aggregates can result in a significant improvement in the biological effectiveness of the applied active ingredient when compared to that achieved with more conventional types of formulation. This enhancement is best demonstrated by reference to the following examples given below.

EXAMPLE A

Use of Insecticide by Soil Application

In certain instances the insect pest attacking a particular plant species does so by attacking the roots of the plant which are embedded in the soil substrate. In these cases the insecticide has to be applied directly to the soil and the criteria which determines the level of control of the pest is depth of penetration into the soil and eveness of distribution within sub-levels within the soil substrate.

In laboratory studies columns of soil were prepared in such a manner that 230 gms of soil having a moisture content of 5 wt % were tamped to give a column height of 8 inches within a 10 inch plastic tube of 1.25 inch internal diameter. The formulation shown in example 10 above, which is in the form of a lipophilic mixed non-ionic surfactant aggregate, was diluted to 0.08% bifenthrin in water and 2 mls of this dilution applied by pipette to the surface of the soil column described above, this was followed immediately by application of 20 mls of double distilled water as an eluent. After standing for 24 hours the plastic tube was split and the column of soil exposed. The soil was then split into 1 inch segments which were then placed in sealed glass jars with 20 ml of HPLC grade methanol and placed in an ultrasonic bath for 30 minutes to extract the bifenthrin. Following the ultrasonication a 2 ml sample of each extraction was placed in a centrifuge vial and centrifuged for 10 minutes at 10,000 rpm to sediment out any extraneous particulate material. The clear supernatant liquid was then injected on to an HPLC column (reverse phase) and the concentrate of bifenthrin present in each 1 inch section of soil determined. In parallel to this a commercial Emulsifiable Concentrate, (EC), formulation of bifenthrin was also diluted in water to 0.08% active ingredient and columns of soil treated in an identical manner to that described above.

The results, which are the mean of five replicates analysed in duplicate with external standard solutions used for calibration of bifenthrin level, are given in tables 9 and 10 below where the results are expressed as % of applied bifenthrin present in each 1 inch segment.

TABLE 9

Distribution of bifenthrin in soil columns
Effect of formulation type: MNSA vs EC

| Soil Depth | % of total bifenthrin in soil | |
|---|---|---|
| (inches) | MNSA | EC |
| 0-1 | 17.97 | 33.7 |
| 1-2 | 22.81 | 31.34 |
| 2-3 | 26.67 | 21.03 |
| 3-4 | 22.64 | 10.61 |
| 4-5 | 8.66 | 3.32 |
| 5-6 | 1.25 | 0 |

TABLE 10

Cumulative distribution of bifenthrin in soil columns
Effect of formulation type: MNSA vs EC

| Cumulative Depth | % of total bifenthrin in soil | |
|---|---|---|
| (inches) | MNSA | EC |
| 0-1 | 17.97 | 33.70 |
| 0-2 | 40.78 | 65.04 |
| 0-3 | 67.45 | 86.07 |
| 0-4 | 90.09 | 96.68 |
| 0-5 | 98.75 | 100 |
| 0-6 | 100 | |

These results clearly demonstrate that the hydrophilic mixed non-ionic surfactant aggregates deposit the active ingredient much more evenly throughout the soil following topical application to the surface when compared to a conventional EC formulation. Moreover, the active ingredient is deposited to much greater depths (32.45% of total active ingredient with MNSA vs 13.93% of total active ingredient with EC into the 3 to 6 inch segment) and this would be expected to give much better control of soil borne insect pests.

In a second experiment the formulation given in Example 5 and contained within a water soluble sachet [PVA film] was diluted in water to give a bifenthrin concentration of 0.08% and this solution used to treat a column of soil as described in the methodology above. The distribution of bifenthrin throughout the column of soil is given in tables 11 & 12 where it is again compared to the standard EC formulation.

TABLE 11

Distribution of bifenthrin in soil columns
MNSA example 5 vs EC

| Cumulative Depth | % of total bifenthrin in soil | |
|---|---|---|
| (inches) | MNSA | EC |
| 0-1 | 8.21 | 33.7 |
| 1-2 | 13.16 | 31.34 |
| 2-3 | 16.21 | 21.03 |
| 3-4 | 21.37 | 10.61 |
| 4-5 | 24.15 | 0 |
| 5-6 | 15.13 | |
| 6-7 | 1.56 | |
| 7-8 | 0.21 | |

TABLE 12

Distribution of bifenthrin in soil columns
MNSA example 5 vs EC

| Cumulative Depth | % of total bifenthrin in soil | |
|---|---|---|
| (inches) | MNSA | EC |
| 0-1 | 8.21 | 33.7 |
| 0-2 | 21.37 | 65.04 |
| 0-3 | 37.58 | 86.07 |
| 0-4 | 58.95 | 96.68 |
| 0-5 | 83.1 | 100 |
| 0-6 | 98.23 | |
| 0-7 | 99.79 | |
| 0-8 | 100 | |

With this formulation with an increased surfactant: bifenthrin ratio we see even better distribution of the active ingredient within the soil to greater depths with the potential for much improved control of soil borne insect pest.

EXAMPLE B

Topical Application to Timbers

Traditionally timbers have been treated in situ by the spray or brush application of solutions of insecticide or fungicide in a petroleum based solvent. Although conventional water based systems such as dilutions (in water) of SC and EC type systems have been examined these proved ineffectual with respect to their poor penetration into the sub surface layers of the timber. In the treatment of timbers by surface application there is a need to have some of the active ingredient deposited at or near the surface in order to protect against infestation of the timber by freshly laid eggs and also to provide a "toxic envelope" extending to a depth of 5-6 mm into the timber in order to eradicate larvae present in the timber. Solvent based systems give this type of deposition pattern when applied to timbers in this manner.

The structure of timber includes an array of capillary tubes with diameters typically in the range of 1-10 microns through which fluids are transported into the wood. Failure of the SC and EC systems will be due, in the main, to the relatively large particle size of the dispersed phase containing the insecticide active ingredient which will be of an order of magnitude that is similar to these capillary tubes.

The mixed non-ionic surfactant aggregates described herein have typical aggregate diameters in the range 10-100 nm (0.01-0.1 microns) and as a consequence we might expect them to behave in a manner similar to a solvent particularly if the surfactant can also allow for effective wetting of the timber surfaces.

In an initial study a bifenthrin mixed non-ionic aggregate formulation as given in example 9 was diluted in water to give a bifenthrin concentration of 0.03% w/w and this was applied to the radial face of blocks of Scots pine sapwood at the rate of 240 mls per square meter. At the same time a commercial sample of an 8% bifenthrin SC formulation was also diluted to the same in use level and applied to Scots pine sapwood blocks at the same rate.

The treated blocks were then left at ambient conditions for 7 days. Thin sections (ca 0.125 mm) of timber were then removed from the timber blocks using a hand plane (sections were weighed and the exact thickness determined using the density of wood in a particular block). These sections were then extracted by ultrasonication for 1 hour in 2 mls of methanol (HPLC grade) and the concentration of insecticide determined analytically by an HPLC method.

In this study the proportion of the applied active ingredient found in the top 0.25 mm if the timber (surface layer) were determined and the results were as shown in Table 13 below.

TABLE 13

Distribution of bifenthrin in surface layer of timbers
treated by topical application
MNSA example vs SC

| Sample | % of bifenthrin in surface layer |
|---|---|
| MNSA | 33.2 |
| SC | 72.4 |

Clearly, as expected, the SC formulation deposits a much greater proportion of its active ingredient into the surface layer and therefore does not penetrate the sub surface of the timber.

In a second study a permethrin based MNSA formulation as given in example 3 above along with a commercial EC formulation were diluted in water to give a permethrin concentration of 0.1% w/w and applied to timber blocks as described above. As a control a solution of 0.1% w/w permethrin dissolved in Shellsol A (naphthenic solvent) was also tested. Sections were taken down to 6 mm and the % of the permethrin in each section determined, the results are given in Table 14 below.

TABLE 14

Deposition profile of permethrin in Scots pine sapwood
following topical application
Effect of formulation type

| Section Depth | % permethrin in section | | |
|---|---|---|---|
| (mm) | Solvent | EC | MNSA |
| 0-1 | 61.2 | 81.9 | 53.5 |
| 1-2 | 15.5 | 15.2 | 24.2 |
| 2-3 | 10.7 | 2.9 | 12.0 |
| 3-4 | 7.8 | | 7.3 |
| 4-5 | 3.9 | | 2.2 |
| 5-6 | 0.9 | | 0.4 |

The MNSA formulation gives a very similar profile as the solvent based solution whereas the EC system gives a much shallower deposition with more than 80% of the ai in the top 1 mm layer.

There is thus described a non-ionic surfactant aggregate, which in the preferred embodiments, allows water insoluble active ingredients to be solubilised or emulsified into a water carrier for delivery, eg. by spraying, as desired, e.g. to a surface or plant. Moreover the preferred embodiments provide the advantage of a lack of phase separation. This lack of phase separation is demonstrated in Table 15 below using results generated as per Table 1 above with an MNSA formulation containing a synthetic pyrethroid insecticide as the active ingredient.

TABLE 15

| Phase Separation following dilution | |
|---|---|
| | MNSA Formulation |
| nominal active ingredient content (wt %) | 0.0127 |
| ai content in Top 10% | 0.0129 |
| active/ingredient actual/nominal | 1.01 |
| active ingredient content in Middle 10% | 0.013 |
| active ingredient actual/nominal | 1.02 |
| active ingredient content in Bottom 10% | 0.0127 |
| active ingredient actual/nominal | 1.00 |

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A non-ionic surfactant emulsion aggregate, the aggregate being in the form of discrete water in oil microemulsion droplets, the aggregate comprising a water insoluble biocidally active ingredient having a required hydrophilic-lipophilic balance (Required HLB), a non-ionic surfactant system, and water, the aggregate having aggregate diameters less than 100 nanometers and being substantially free of organic solvent, the non-ionic surfactant system comprising first and second non-ionic surfactants, the first non-ionic surfactant comprising at least one primary non-ionic surfactant being soluble in water and having an aqueous cloud point greater than 25° C., and the second non-ionic surfactant comprising at least one non-ionic cosurfactant being insoluble in water and having an aqueous cloud point less than 25° C., proportions of the primary surfactant and the cosurfactant matching the Required HLB of the active ingredient, wherein the water is present in the non-ionic surfactant aggregate in an amount in the range of 0.1 wt % to 6.8 wt % and wherein the surfactant system is present in the non-ionic surfactant aggregate in an amount in the range of 57.5 wt % to 75.34 wt %, the active ingredient is present in an amount of between 10 wt % and 15 wt %, and the non-ionic surfactant aggregate has no tendency to phase separate across a temperature range of 0 to 50° C. at a water hardness of 0 to 1,000 ppm calcium carbonate.

2. A non-ionic surfactant aggregate according to claim 1, wherein the mass fractions of the active ingredient [Pact]m, total non-ion surfactant [Psurf]m, non-ionic cosurfactant [Pcos]m are as follows:
active ingredient mass fraction, [Pact]m: 0.002 to 0.431
total non-ionic surfactant mass fraction [Psurf]m: 0.569 to 0.998
non-ionic cosurfactant mass fraction [Pcos]m: 0.07 to 0.787.

3. A non-ionic surfactant aggregate according to claim 1 substantially free of ionic surfactants.

4. A non-ionic surfactant aggregate according to claim 1 wherein the biocide is selected from one or more of an insecticide, a fungicide, a herbicide, a nematicide, or a miticide.

5. A non-ionic surfactant aggregate according to claim 1 wherein the biocide is an insecticide and the insecticide is selected from one or more of a pyrethroid, an organophosphate compound, a phenyl ether, a benzoylurea, a carbamate, a nicotinoid, or a pyridinecarboxamide.

6. A non-ionic surfactant aggregate according to claim 1, wherein the biocide is an insecticide and the insecticide is selected from one or more of a pyrethroid, an organophosphate compounds, a phenyl ether, a benzoylurea, a carbamate, a nicotinoid, or a pyridinecarboxamide wherein: where the insecticide comprises a pyrethroid, the pyrethroid is selected from one or more of bifenthrin, zeta-cypermethrin, alpha-cypermethrin, tetra-methrin, lambda-cyhalothrin, fenvalerate, cyfluthrin, bio-resmethrin, permethrin, or deltamethrin; where the insecticide comprises an organophosphate compound, the organophosphate compound is selected from one or more of chlorpyrifos-ethyl, chlorpyrifos-methyl, pirimiphos-methyl, or fenitrothion; where the insecticide comprises a phenyl ether, the phenyl ether comprises pyriproxyfen where the insecticide comprises a benzoylurea; the benzoylurea comprises flufenoxuron where the insecticide comprises a carbamate; the carbamate comprises fenoyxcarb, or carbosulfan; where the insecticide comprises a nicotinoid, the nicotinoid comprises acetamiprid; where the insecticide comprises a pyridinecaboxamide, the pyridinecaboxamide comprises flonicamid.

7. A non-ionic surfactant aggregate according to claim 1, wherein the non-ionic surfactant system comprises two or more surfactants selected from a group consisting of alkoxylated alcohols, amine ethoxylate, ester ethoxylate, castor oil ethoxylate, fatty acid ethoxylate, amide ethoxylate, ethylene oxide-propylene oxide block copolymers, alkoxylated oils, alkoxylated vegetable oils, and alkoxylated fatty acids.

8. A non-ionic surfactant aggregate according to claim 1 wherein the non ionic surfactant system comprises an alcohol ethoxylate, and has a straight or branched chain.

9. A non-ionic surfactant aggregate according to claim 1 wherein the non ionic surfactant system comprises alkoxylated alcohols, and the alkoxylated alcohol having a chain length of 9 to 13 carbon atoms.

10. A non-ionic surfactant aggregate according to claim 1 wherein the non-ionic surfactant system comprises an ethylene oxide-propylene oxide block copolymers having an ethylene oxide content in the range of 10 wt % to 20 wt %.

11. A non-ionic surfactant aggregate according to claim 1 wherein the non-ionic surfactant system comprises an alkoxylated castor oil.

12. A non-ionic surfactant aggregate according to claim 1 wherein the non-ionic surfactant system comprises alkoxylated vegetable oils and the alkoxylated vegetable oil comprises an ethoxylated castor oil, having an ethylene oxide content of 5 to 60 moles ethylene oxide per molecule.

13. A non-ionic surfactant aggregate according to claim 1, wherein the non-ionic surfactant aggregate comprises a hexagonal, lamella, cylindrical or spherical structure.

14. A non-ionic surfactant aggregate according to claim 1, wherein the total surfactant mass fraction ratio [Psurf]m is in the range 0.569 to 0.96.

15. A packaged aggregate comprising a water soluble packaging member containing a non-ionic aggregate as claimed in claim 1.

16. A packaged product according to claim 15 wherein the water soluble packaging member comprises a sealed sachet.

17. A packaged product according to claim 15 wherein the water soluble packaging member is formed of a water soluble plastics material.

18. A packaged product according to claim 17 wherein the water soluble packaging member is formed of polyvinylalcohol (PVA).

19. A non-ionic surfactant aggregate according to claim 9, wherein the alkoxylated alcohol comprises 2 to 12 moles ethylene oxide per molecule.

20. A non-ionic surfactant aggregate according to claim 1, wherein and the cosurfactant mass fraction ratio $[Pcos]m$ is in the range 0.07 to 0.787.

21. A non-ionic surfactant aggregate according to claim 1, wherein the aggregate is clear.

22. A non-ionic surfactant aggregate according to claim 1, wherein the aggregate is free of anionic surfactants.

* * * * *

UNITED STATES PATENT AND TRADEMARK OFFICE
CERTIFICATE OF CORRECTION

PATENT NO. : 9,433,207 B2
APPLICATION NO. : 11/576795
DATED : September 6, 2016
INVENTOR(S) : Dawson et al.

It is certified that error appears in the above-identified patent and that said Letters Patent is hereby corrected as shown below:

In the Specification

Column 6, Line 19  "...polyvinylacohol..." should be --polyvinylalcohol--

Column 7, Line 42  "Pluronic PE10100 (EG-PO copolymer cosurfactant..." should be --Pluronic PE10100 (EO-PO copolymer cosurfactant...--

Column 9, Line 64  "Neodol 91-2.5 (alcohol ethoxy late cosurfactant,..." should be --Neodol 91-2.5 (alcohol ethoxylate cosurfactant,--

Column 12, Line 45  "$Rh=kT/6\pi\eta nD$" should be --$Rh=kT/6\pi\eta D$--

Column 14, Line 38  " ...extend on the ratio..." should be --extent on the ratio--

Column 15, Line 2  "...These other may be present..." should be --These others may be present--

In the Claims

Column 27, Claim 20, Line 16  "...wherein and the cosurfactant..." should be --wherein the cosurfactant--

Signed and Sealed this
Third Day of January, 2017

Michelle K. Lee
*Director of the United States Patent and Trademark Office*